United States Patent [19]

Embro

[11] Patent Number: 5,908,640

[45] Date of Patent: Jun. 1, 1999

[54] VETERINARY COMPOSITIONS FOR TREATING EPIDERMAL IRRITATIONS

[76] Inventor: William J. Embro, 832 NW. 57th St., Gainesville, Fla. 32605

[21] Appl. No.: 08/900,776

[22] Filed: Jul. 25, 1997

[51] Int. Cl.[6] ............................. A01N 59/16; A01N 59/10
[52] U.S. Cl. ............................................ 424/650; 424/673
[58] Field of Search ...................................... 424/650, 673

[56] References Cited

U.S. PATENT DOCUMENTS 5,098,716  3/1992  Embro ...................................... 424/650

FOREIGN PATENT DOCUMENTS 565495   10/1993   European Pat. Off. .
9325211  12/1993   WIPO .

*Primary Examiner*—José G. Dees
*Assistant Examiner*—Alton Pryor

[57] ABSTRACT

A method and treatment is described for treating epidermal irritations due to insect bites and parasitic manifestations by applying a non-toxic composition of the chemical compound stannous fluoride.

4 Claims, No Drawings

VETERINARY COMPOSITIONS FOR TREATING EPIDERMAL IRRITATIONS

CROSS-REFERENCE TO RELATED APPLICATION

Not Applicable

STATEMENT OF FEDERALLY SPONSORED RESEARCH OR DEVELOPMENT

Not Applicable

REFERENCE TO MICROFICHE APPENDIX

Not applicable

BACKGROUND OF THE INVENTION

The present invention relates to a treatment and prevention of insect bites and parasitic manifestations that lead animals to rub, scratch, or bite at a body site whereby the result may lead to loss of hair, infection and scarring. It is well established that animals react to insect bites and parasite infections by scratching, biting or rubbing which often causes the animal to lose hair and may also cause serious fungal and bacterial infections. In the Equine and Bovine industry, loss of bodily hair can depreciate the value of the animal when presented to potential buyers. Dogs and cats are constantly plagued with fleas, mites and lice (a condition that causes scratching and biting). Other pets including birds, rodents, and the like either peck or bite themselves in order to get relief from irritations associated with insect bites and other parasites. More particularly, the invention relates to the topical application of stannous fluoride for the treatment of such conditions.

A large number of pharmaceuticals have been developed for administration to animals suffering from pain, itching or inflammation which accompany insect bites and parasitic infections. Antihistamines, analgesics, corticosteroids, DMSO and astringents dressings are typical of such treatments. However, it is often the case that such treatments are either ineffective or marginally effective, have associate undesirable side effects, or are prohibitively expensive, especially when long term administration is required.

It is, therefore, an objective of the present invention to provide a safe and inexpensive treatment and prevention of insect bites, mites, lice and other skin conditions such as ringworm leading to scratching, rubbing, and biting which cause hair loss and epidermal abrasions and infections.

SUMMARY OF THE INVENTION

The present invention meets this objective by providing a treatment which includes the topical application of stannous fluoride preparation. A non-toxic amount of stannous fluoride is incorporated into a pharmaceutical carrier, such as a gel, ointment, cream, lotion or the like, and applied to the affected site. Preferably, the stannous fluoride is provided in a concentration ranging from about 0.1 wt. % to about 8 wt. %. Most preferably, the stannous fluoride is applied as a 0.4% $SnF_2$ glycerin-based gel. The frequency of application may range anywhere from one to six times a day or on an as needed basis. The course of the therapy typically ranges from one to six times a day but may be continued as long as required for complete relief.

DETAILED DESCRIPTION OF THE INVENTION

A non-aqueous stannous fluoride gel is prepared by solubilizing $SnF_2$ in anhydrous glycerin at approximately 150° F. for four hours. The resulting gel is a stable solution having indefinite shelf life that is ideal for topical application to epidermal and muco-epidermal tissue. As the following examples demonstrate, stannous fluoride prevents animals from scratching and rubbing epidermal sites associated with insect bites or parasitic infections. Although the mechanism of action is not clearly understood, it is hypothesized that both tin ($Sn^{++}$) and fluoride ($F^-$) ions interact together and affect nerve action potentials, histamine release, cellular enzyme systems and vascular systems, all of which can influence the itching and inflammation cause by insect bites and parasitic manifestations. Furthermore, it is proposed that the active ingredient stannous fluoride can create an environment that inhibits the livelihood of parasitic organisms.

EXAMPLE 1

Ten horses exhibiting intermittent rubbing of mane, tail, neck, leg or side (Summer itch) were relieved of the discomfort when a solution of 0.4% $SnF_2$ gel was administered to the affected areas 2 to 3 times daily.

EXAMPLE 2

Five dogs washed with a solution of 0.1% Stannous fluoride inhibited flea infestation and prevented scratching.

EXAMPLE 3

Five horses suffering from ringworm with application of 1.64% Stannous Fluoride gel two times daily. After one week of application, the horses did not rub and the ringworm infestation site was eliminated.

What is claimed is:

1. A method of treating and preventing an epidermal irritation in a non-human animal comprising administering an effective non-toxic amount of stannous fluoride in combination with a pharmaceutically acceptable carrier.

2. The method of claim 1 is further characterized in that stannous fluoride is provided in a concentration ranging from about 0.1 weight percent to about 8 weight percent.

3. The method of claim 1 wherein the pharmaceutical carrier is a gel, ointment, cream, mist, or lotion.

4. The method of claim 1 is further characterized in that stannous fluoride is applied as a 0.4 or 1.64 weight percent glycerin-based rinse or gel.

* * * * *